(12) United States Patent
Lunan

(10) Patent No.: US 6,381,869 B1
(45) Date of Patent: May 7, 2002

(54) FLOWER PRESS

(75) Inventor: Robert R. Lunan, Kemptville (CA)

(73) Assignee: Lee Valley Tools, Ltd. (CA)

( * ) Notice: Subject to any disclaimer, the term of this patent is extended or adjusted under 35 U.S.C. 154(b) by 0 days.

(21) Appl. No.: 09/817,650

(22) Filed: Mar. 26, 2001

Related U.S. Application Data

(63) Continuation of application No. 09/340,246, filed on Jul. 1, 1999, now Pat. No. 6,237,245.

(51) Int. Cl.[7] ................................................. F26B 9/04
(52) U.S. Cl. ............................... 34/146; 34/259; 34/70; 34/71; 34/95; 34/144; 100/92; 100/302; 100/297; 219/735; 219/757
(58) Field of Search ............................... 34/71, 69, 70, 34/95, 80, 143, 144, 145, 146, 259, 265, 398, 420; 100/92, 305, 295, 296, 297; 219/733, 734, 735, 757, 756, 762

(56) References Cited

U.S. PATENT DOCUMENTS 5,948,311 A * 9/1999 Beecroft et al. ............ 219/762

* cited by examiner

*Primary Examiner*—Pamela Wilson
(74) *Attorney, Agent, or Firm*—Kristin L. Johnson; John S. Pratt; Kilpatrick Stockton LLP

(57) ABSTRACT

A device for pressing and drying organic materials. The organic material is inserted between two sheets of thin cloth which are, in turn, sandwiched between two thick felt pads. These pads are then sandwiched between platens made from inorganic material. The assembly is heated, resulting in a pressed and dried organic material.

4 Claims, 1 Drawing Sheet

FLOWER PRESS

This application is a continuation of U.S. application Ser. No. 09/340,246, filed Jul. 1, 1999, now U.S. Pat. No. 6,237,245.

FIELD OF THE INVENTION

This invention relates to pressed, dried flowers and other organic materials and to presses for drying such materials.

BACKGROUND OF THE INVENTION

It has long been known to dry and press flowers and other organic materials by sandwiching the flower or material between sheets of absorbent material (such as cloth or felt) which are backed by more rigid materials and applying pressure. The use of books to dry and press flowers is one example of this technique. Eventually, the flower will dry. However, problems of absorption of the excess moisture from this drying process arise. Moreover, such conventional approaches are time-consuming and lead to color loss in the pressed material.

Microwave ovens have been used to facilitate the drying and pressing process. For instance, an article from the *London Times* entitled *How to Bloom in a Basket* (Jan. 21, 1990), heralding a weekend course on pressing and drying flowers, discloses sandwiching flowers between blotting paper and newspaper and placing the assembly in a flower press and then in a microwave oven. *Glorious Pressed Flower Projects* by Cellestine Hannemann (1991) also discloses use of a microwave oven in the flower drying process. In *Glorious Pressed Flower Projects*, the flowers are placed on a polyester pad, and a flat sheet of chipboard is pressed atop the flowers. Marble or glass weights are used to flatten and weigh down the sandwich of flowers. The sandwich is then placed in a microwave oven and heated. Australian Patent No. 695560 to Beecroft describes a flower press in which a flower is sandwiched between thin absorbent sheets backed by felt pads. The pads are then sandwiched between plastic platens held together by clips. The assembly is then placed in a microwave oven.

SUMMARY OF THE INVENTION

This invention is a device for pressing and drying organic materials in a microwave oven. The organic material is inserted between two sheets of thin cloth which are, in turn, sandwiched between two thick felt pads. These pads are then sandwiched between platens made from inorganic material, preferably ceramic, such as unglazed terra cotta. The assembly is placed in a microwave oven and heated, resulting in a pressed and dried organic material.

This invention vastly improves the microwave drying and pressing processes of the prior art. Terra cotta platens are inexpensive and easily molded into desired shapes. Moreover, because some ceramics, such as terra cotta, are not fully microwave transparent (as opposed to the plastic platens of the prior art which are fully microwave transparent, resulting in over-drying of the flower), the drying process is tempered, rendering cracking and scorching of the flower or plant less likely and enhancing the color-retention of the organic material. In addition, ceramics like terra cotta, unlike plastic, are a moisture absorbent material. The moisture from the drying process is therefore transferred from the felt backing to the ceramic platens, which moderates the drying process. Furthermore, the weight of the platens obviates the need for separate weights or clips to secure and press the two platens together.

The design of the platens also facilitates the drying and pressing process. The platens are ventilated with holes to allow for moisture to escape during the drying process. The corners of the platens have raised feet which support the assembly, preventing contact between the lower platen and the microwave oven floor. This allows for vapors to escape from the lower platen as well as the top platen, thus facilitating the drying process. Moreover, rubber bands may be looped around the platens to increase the pressing pressure during the drying process and to secure the platens together for storage purposes.

DETAILED DESCRIPTION OF THE DRAWINGS

Figure 1:
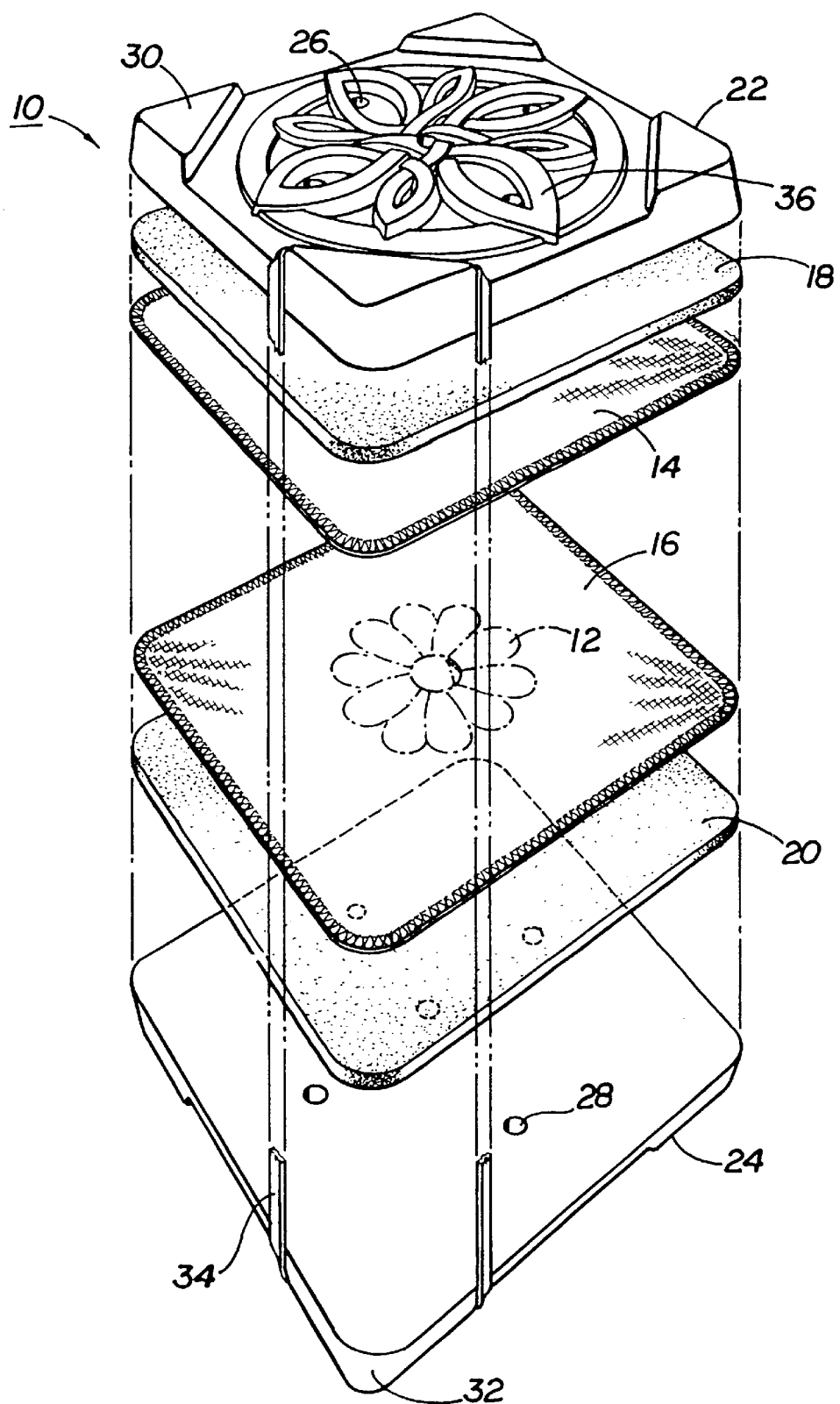
FIG. 1 is an exploded perspective view of the flower press.

FIG. 1 illustrates one embodiment of the flower press 10 of this invention. A flower or other organic material 12 is inserted between two cloth sheets 14, 16. While the sheets 14, 16 may be made from a variety of absorbent materials including cotton and linen or various blends of each, a cotton/polyester blend is particularly effective. The cloth sheets 14, 16 are, in turn, inserted between two pads 18, 20. Felt, wool felt in particular, while only one of a variety of possible absorbent materials from which to manufacture the pads 18, 20, has proven to be particularly useful in this application. The pads 18, 20 are then placed between platens 22, 24, and the resulting assembly is placed in the microwave oven and heated to dry and press the flower 12.

The platens 22, 24 may be made from a variety of inorganic materials possessing suitable physical properties including structural integrity, substantial weight, and adequate strength. The platens should be relatively dense and therefore heavy. A density of at least about 1.5 g/cm$^3$ is preferred. Additionally, the chosen material, while being partially transparent to microwave radiation, need not be fully microwave transparent. It is also desirable that the chosen material have the capacity to absorb moisture and to include passages for moisture vapors. The passages permit rapid moisture removal, but the absorption moderates the process so that drying does not occur too rapidly, as can occur with moisture impermeable materials. Particularly useful materials possessing these properties include porous ceramics manufactured, for instance, from clay, such as unglazed terra cotta.

The platens 22, 24 are ventilated with holes 26, 28 to allow moisture to escape during the drying process. The corners of the platens 22, 24 are equipped with raised feet 30, 32 which perform two important functions. First, the feet 30, 32, which support the assembly, prevent contact between the lower platen 24 and the microwave oven floor, thus allowing vapors resulting from the drying process to escape through the holes 28 of the lower platen 24. The feet 30, 32 also facilitate stability of the press 10. When a rubber band or other securing device 34 is looped around the platens 22, 24 to increase the pressing pressure during the drying process and to secure the platens 22, 24 together for storage, the feet 30, 32 of the platens 22, 24 prevent the securing device 34 from slipping off the platens 22, 24. Finally, an ornamental design 36 adorns the platens 22, 24, giving this functional device a much more aesthetically pleasing appearance.

The foregoing is provided for purposes of illustrating, explaining, and describing embodiments of the present invention. Further modifications and adaptations to these embodiments will be apparent to those skilled in the art and may be made without departing from the scope or spirit of the invention.

I claim:

1. A press for drying and pressing organic materials, comprising multiple layers including an outer layer and an inner layer, wherein the outer layer comprises two platens comprising moisture absorbent inorganic material and the inner layer comprises organic material.

2. The press of claim 1, further comprising at least one middle layer positioned between the outer layer and the inner layer.

3. The press of claim 2, wherein the at least one middle layer comprises two pads of moisture permeable material.

4. A press for drying and pressing organic materials, comprising a first layer comprising at least two cloth sheets sandwiched between a second layer comprising at least two felt pads which are in turn sandwiched between a third layer comprising at least two platens comprising inorganic material, wherein the organic materials are positioned between the platens.

* * * * *